United States Patent [19]

Ryan et al.

[11] Patent Number: 4,622,845
[45] Date of Patent: Nov. 18, 1986

[54] METHOD AND APPARATUS FOR THE DETECTION AND MEASUREMENT OF GASES

[75] Inventors: Frederick M. Ryan, Loyalhanna Township, Westmoreland County, Pa.; Donald W. Feldman, Los Alamos, N. Mex.

[73] Assignee: Westinghouse Electric Corp., Pittsburgh, Pa.

[21] Appl. No.: 714,582

[22] Filed: Mar. 21, 1985

[51] Int. Cl.⁴ .......................................... G01N 21/00
[52] U.S. Cl. ........................................................ 73/24
[58] Field of Search .......................... 73/24; 250/343; 356/437

[56] References Cited

U.S. PATENT DOCUMENTS 3,948,345  4/1976  Rosencwaig ............................ 73/24

FOREIGN PATENT DOCUMENTS 2089041  6/1982  United Kingdom .................... 73/24

OTHER PUBLICATIONS

L. B. Kreuzer, "Ultralow Gas Concentration Infrared Absorption Spectroscopy", *Journal of Applied Physics*, vol. 42, No. 7, pp. 2934–2943, Jun. 1971.
"Nitric Oxide Air Pollution: Detection by Optoacoustic Spectroscopy", *Science*, vol. 173, pp. 45–46, Jul. 1971.

Primary Examiner—Stephen A. Kreitman
Attorney, Agent, or Firm—Thomas R. Trempus

[57] ABSTRACT

The invention provides an apparatus for the detection of a selected species in a gas sample and includes a photo-acoustic detector coupled to an infrared radiation source with an acousto-optic tunable filter disposed between the source of infrared radiation and photo-acoustic detector. This combination is capable of measuring concentrations of controlled vapors in the parts-per-million range. These measurements may be performed in a few seconds via the portable gas detection and measurement device of this invention.

4 Claims, 1 Drawing Figure

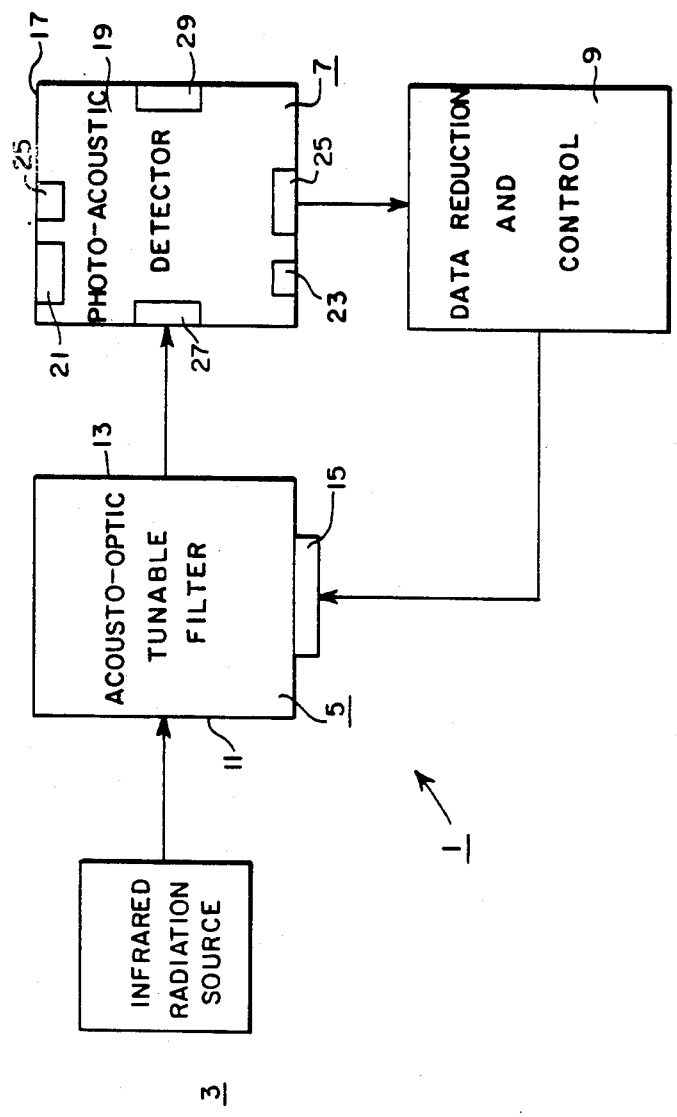

METHOD AND APPARATUS FOR THE DETECTION AND MEASUREMENT OF GASES

BACKGROUND OF THE INVENTION

The present invention relates to gas detectors generally, and, more particularly, the invention is directed to an apparatus and method for the detection and measurement of gases in low concentration.

A large and growing market exists for analytical devices which can be used to analyze reaction products of a wide variety of industrial processes. For applications such as the detection of toxic gases, it is necessary to measure the concentration of the species of interest in very low concentrations, typically as low as parts per million. A conventional approach for measuring the concentrations of a gas of interest is to put a sample of ambient air in an optical cell and measure the magnitude of absorption of specific molecules of interest at a specific wavelength in the infrared. Since the concentration of the molecules is expected to be quite low, the infrared absorption to be measured is also very low. In order to increase the magnitude of the absorption, a long path optical cell is typically employed in which, by the use of multiple reflections between mirrors, effective path lengths as long as 20 meters may be achieved. The disadvantage of this approach is that the multiple pass optical cell is expensive, large, and heavy. It does not therefore lend itself to the portability necessary for a device of the type desired for compliance with O.S.H.A. regulations covering permissible levels of these gases in the workplace.

Only one such cell for gas measurement is employed in commercially available instruments so that the cell must be first filled with filtered air to establish a "reference" absorption, then emptied and refilled with ambient air. The absorption is measured a second time and the two absorption measurements are compared to determine the absorption of the gaseous species of interest. This procedure is obviously very time consuming and very susceptible to errors due to drift in the electronics in between measurements. If the concentration of the gaseous species to be measured is very low, the theoretical difference between the two measurements is very small. Two large transmission values must therefore be subtracted in order to yield a small difference signal, and any drift in the large transmission values will mask the true absorption value.

Another weakness in the approach used in presently available instruments is that interference filter wheels are employed to tune a source of infrared light to the appropriate wavelength for the absorption measurement. While the interference filter wheel can achieve the high energy throughput of infrared desired for this type of measurement, it achieves a very low resolution of specific wavelengths in the infrared. This result in interfering absorptions between various gaseous species and again results in errors in measurement.

It is therefore an object of this invention to provide an improved apparatus for the detection and measurement of a concentration of a gaseous species in very low concentrations.

It is another object of this invention to provide a process for the detection and measurement of gaseous species.

It is yet another object of this invention to provide a compact, portable gas detection and measurement device with the capabilities to comply with O.S.H.A. regulation measurements of toxic species.

SUMMARY OF THE INVENTION

The invention provides a process and an apparatus for the detection of a select species in a gas sample taken from an ambient environment. The detector apparatus comprises in combination a photo-acoustic detector, a source for infrared radiation and an acousto-optic tunable filter. The photo-acoustic detector includes walls defining an enclosed chamber with the valve means operatively associated with the walls for introducing a gas sample into the chamber and for vacating the gas sample therefrom. The chamber walls include means for detecting an acoustic disturbance within the chamber and window means on opposite sides of the chamber for the passage of infrared radiation therethrough. An infrared radiation source is operatively associated with the photo-acoustic detector to provide infrared radiation for passage through said chamber. The acousto-optic tunable filter is disposed between the photo-acoustic detector and the infrared radiation source. The acousto-optic tunable filter (AOTF) comprises an optically aligned acousto-optic crystal through which infrared radiation is passed at a predetermined angle relative to the crystal optic axis. An acoustic transducer means is coupled to a variable frequency rf energy source and to the acousto-optic crystal in order to launch acoustic waves into the crystal to interact with a selected narrow bandwidth portion of the infrared radiation. This interaction between the acoustic waves and the infrared radiation distinguishes the selected narrow bandwidth portion from the remaining infrared radiation. The narrow bandwidth portion is a function of the frequency of the rf energy and the acoustic waves. The selected narrow bandwidth portion of infrared radiation is directed through the chamber windows for interaction with the sample gas in the chamber. The interaction generates an acoustic disturbance in the presence of a predetermined selected species within the chamber.

BRIEF DESCRIPTION OF THE DRAWING

The above as well as other features and advantages of the present invention can be appreciated through consideration of the detailed description of the invention in conjunction with the sole FIGURE which is a schematic illustration of an embodiment of the gas detector apparatus all according to the teachings of the present invention.

DESCRIPTION OF THE PREFERRED EMBODIMENT

The gas detection apparatus of this invention incorporates an acousto-optic tunable filter (AOTF) and a photo-acoustic (PA) detector cell. The AOTF is constructed from a suitable material such as thallium arsenide selenide, and functions as a high throughput source of infrared selective filtering of high resolution. A non-collinear configuration in an acousto-optic tunable filter is taught by U.S. Pat. No. 4,052,121 to Chang. In allowed U.S. patent application Ser. No. 345,123, now U.S. Pat. 4,490,845, entitled "An Automated Acousto-Optic Infrared Analyzer" to Steinbruegge et al., which is assigned to the assignee of the present invention and which is incorporated herein by reference, a system is described in which a narrow band pass tunable acousto-optic filter can be selectively tuned by predetermined rf frequency signals to selectively transmit the narrow bandpass of interest which corresponds to a specific molecular species for identification and analysis. The system described in this allowed patent application includes a microcomputer in associated memory function to measure and compare detected signals from an infrared detector which converts the filtered infrared signal to an electrical signal. The memory provides control signals for the computer and for controlling the sequence and frequency of rf energy applied to tune the filter. In this way, the near to mid range infrared can be analyzed for absorption bands corresponding to predetermined molecular species, and a feedback signal generated to control a combustion process, or the like. The use of an acousto-optic tunable filter in this invention permits rapid electronic tuning of the filter to a selected infrared bandpass via the acousto-optic interaction with infrared radiation passed through the crystal.

The photo-acoustic (PA) detector is a relatively new device for measuring trace gas absorptions. It utilizes the fact that optical energy which is absorbed by the excitation of molecular vibrations in the infrared, is rapidly conveyed into heat and hence into pressure waves in the medium. Thus, if the source of infrared is modulated at a given frequency, the pressure waves form sound waves of that frequency and may be detected by acoustic transducer, i.e., microphones. The signal produced is proportional to the energy absorbed. If the absorbing medium is a gas in which the absorbing species is at a low level, the acoustic energy produced will be proportional to the concentration of the absorbing species and to the intensity of the incident infrared light. Applicants have described that when the light source is tunable through the use of an acousto-optic tunable filter, the species may be identified by their characteristic infrared absorption wavelengths. Thus, a photo-acoustic detector along with a tunable source of infrared may be used to identify and measure the concentrations of any number of different gaseous species present in a background gas such as air.

The photo-acoustic detector can exist in a variety of configurations. For gas detection, the medium may be contained in a chamber with windows to admit the infrared light, and with acoustic detectors in the walls to detect the absorbed energy. In order to increase the sensitivity, the chamber may be made to be acoustically resonant at the modulation frequency of the infrared light source. An excellent discussion of photo-acoustic spectroscopy can be found in an article entitled "Photo-Acoustic Spectroscopy" by West et al. in review of Scientific Instrumentation Volume 54 (7), July 1983, the contents of which are incorporated herein by reference as if fully set forth herein. The use of photo-acoustic detection provides several distinct advantages over detection by the more conventional absorption methods. The detection element is a microphone, thus expensive infrared detectors are not needed. The signal produced is proportional to the species concentration. Therefore, one does not need to detect a small change in a large signal as is the case for conventional optical absorption techniques as described in the background portion of this document. A photo-acoustic detector system can be compact and light-weight and hence lend itself to portable instrumentation.

The acousto-optic tunable filter and photo-acoustic detector are used in combination with a broad band source of infrared radiation. A preferred source of infrared radiation is a Nernst glower which provides a broad band infrared radiation for use in this system, or a silicon carbide globar. The high energy throughput and wavelength resolution of AOTF filters in the infrared has been described in the literature and can be found in the article entitled "Automated AOTF Infrared Analyzer" Steinbruegge et al., SPIE Volume 268, page 160, 1981, the contents of which are incorporated herein by reference.

Turning now to the sole figure, the acousto-optic tunable filter in combination with a photo-acoustic detector according to this invention is generally indicated by the reference character 1. The major components of this system include the infrared radiation source 3, the acousto-optic tunable filter 5, the photo-acoustic detector sampler 7 and the data reduction and control means 9. As previously indicated, the infrared radiation source 3 is preferably a broadband source of infrared radiation such as a Nernst glower. The acousto-optic tunable filter which is optically aligned between the infrared radiation source 3 and the photo-acoustic detector 7, includes an optical input face 11, an optical output face 13 and a transducer means 15 disposed on at least one side of the acousto-optic filter in order to provide a non-collinear filter. The transducer means 15 is coupled to a variable frequency rf energy source which is included in the data reduction and control means 9.

The photo-acoustic detector 7 includes walls 17 defining an enclosed chamber 19 with valve means 21 and 23 operatively associated with the walls 17 for introducing a gas sample into the chamber 19 and for vacating the gas sample therefrom. The chamber walls 17 include means 25 for detecting an acoustic disturbance within the chamber 19 and window means 27 and 29 on opposite sides of the chamber for the passage of infrared radiation therethrough. The detection means 25 are in electrical communication with the data reduction and control means 9 for processing thereby.

The acousto-optic tunable filter combined with a photo-acoustic detector as described herein has been constructed and operated as a trace gas detection system. The infrared source was a small coiled nichrome heater wire, operating at 1200° C. with a parabolic mirror which focused the light into the acousto-optic tunable filter. The acousto-optic tunable filter had a useful wavelength tuning range of between 1.5 to 16 micrometers. The narrow band light from the filter entered the photo-acoustic cell through the windows which are transparent in the infrared. The microphones were disposed so as to cancel out external vibrations and to reduce background noise. The photo-acoustic chamber in this embodiment is resonant at 4 kHz and the AOTF is pulsed at the same frequency. The control system can be one which scans the wavelength range to acquire a complete absorption, or one that jumps to selected wavelengths to measure concentrations of predetermined gaseous species. The system has been tested with methane and benzene in its performance is consistent with theoretical predictions of performance. The arrangement described and illustrated schematically herein is capable of measuring the concentrations of OSHA-controlled vapors in the parts-per-million range. These measurements may be performed in a few seconds as compared to the typical extended times of between five and ten minutes required using conventional absorption trace gas analyzers.

What has been described is a unique combination of a source of broad band infrared light, an acoustic-optic filter to selectively pass certain wavelengths of that infrared light, and a photo-acoustic detector combined to form a superior instrument for the detection and measurement of gases in low concentration.

What is claimed is:

1. An apparatus for the detection of a selected species in a gas sample comprising:
    a photo-acoustic detector means including walls defining an enclosed chamber with valve means operatively associated with said walls for introducing the gas sample into said chamber and for vacating the gas sample therefrom, and with means for detecting an acoustic disturbance within said chamber, and with window means on opposite sides of said chamber for the passage of infrared radiation therethrough, said enclosed chamber being resonant at 4 kHz;
    an infrared radiation source means operatively associated with said photo-acoustic detector means wherein a narrow bandwidth portion of infrared radiation is directed through said chamber for interaction with the sample gas in said chamber to generate an acoustic disturbance within said chamber in the presence of a selected species; and
    an acousto-optic tunable filter disposed between said photo-acoustic detector means and said infrared radiation source means comprising an optically aligned acousto-optic crystal through which infrared radiation is passed, an acoustic transducer means coupled to a variable frequency energy source pulsed at a rate of 4 kHz and to the acousto-optic crystal in order to pulse said acousto-optic tunable filter at a rate of 4 kHz at a selected frequency to launch acoustic waves in the crystal in order to interact with a selected narrow bandwidth portion of the infrared radiation to make said portion distinguishable from the remaining infrared radiation, which narrow portion is a function of the selected frequency of the rf energy and the acoustic waves launched into said crystal wherein the acoustic disturbance within said chamber is a pulsed disturbance at a rate of 4 kHz.

2. The apparatus according to claim 1, wherein the acousto-optic tunable filter includes a thallium arsenic selenide crystal.

3. The apparatus according to claim 1, wherein the acousto-optic tunable filter has a tuning range of between about 1.5 to 16 micrometers.

4. A method for detecting a selected species in a gas sample taken from an ambient environment comprising the steps of:
    introducing a gas sample into a photo-acoustic detector means including walls defining an enclosed chamber resonant at 4 kHz with valve means operatively associated with said walls for introducing the gas sample into said chamber and for vacating the gas sample therefrom, and with means for detecting an acoustic disturbance within said chamber, and with window means on opposite sides of said chamber for the passage of infrared radiation therethrough;
    providing an infrared radiation source means operatively associated with said photo-acoustic detector means wherein a narrow bandwidth portion of pulsed infrared radiation is directed through said chamber for interaction with the sample gas in said chamber to generate a pulsed acoustic disturbance within said chamber in the presence of a selected species; and
    disposing an acousto-optic tunable filter between said photo-acoustic detector means and said infrared radiation source means, said acousto-optic tunable filter comprising an optically aligned acousto-optic crystal through which infrared radiation is passed, an acoustic transducer means coupled to a variable frequency energy source pulsed at a rate of 4 kHz and to the acousto-optic crystal in order to pulse said acousto-optic tunable filter at a rate of 4 kHz at a selected frequency to launch acoustic waves in the crystal in order order to interact with a selected narrow bandwidth portion of the infrared radiation to make said portion distinguishable from the remaining infrared radiation, which narrow bandwidth portion is a function of the selected frequency of the rf energy and the acoustic waves launched into said crystal wherein the acoustic disturbance within said chamber is a pulsed disturbance at a rate of 4 kHz and wherein a detected disturbance is proportional to the species concentration in the gas sample introduced into the photo-acoustic detector means.

* * * * *